United States Patent
Hubschman et al.

(10) Patent No.: US 8,954,132 B2
(45) Date of Patent: Feb. 10, 2015

(54) METHODS AND SYSTEMS FOR GUIDING AN EMISSION TO A TARGET

(76) Inventors: Jean P. Hubschman, Beverly Hills, CA (US); Steven Schwartz, Los Angeles, CA (US); Jason Wilson, Santa Monica, CA (US); Tsu-Chin Tsao, Manhattan Beach, CA (US)

(*) Notice: Subject to any disclaimer, the term of this patent is extended or adjusted under 35 U.S.C. 154(b) by 1179 days.

(21) Appl. No.: 12/704,947

(22) Filed: Feb. 12, 2010

(65) Prior Publication Data

US 2011/0201939 A1 Aug. 18, 2011

(51) Int. Cl.
*A61B 5/00* (2006.01)
*G06T 7/00* (2006.01)
*G06T 7/20* (2006.01)

(52) U.S. Cl.
CPC ............ *G06T 7/0046* (2013.01); *G06T 7/2046* (2013.01); *G06T 2207/10016* (2013.01); *G06T 2207/10048* (2013.01); *G06T 2207/10056* (2013.01); *G06T 2207/10101* (2013.01); *G06T 2207/20148* (2013.01); *G06T 2207/30096* (2013.01); *G06T 2207/30244* (2013.01)
USPC ........................................... 600/427

(58) Field of Classification Search
USPC ................... 600/407, 410, 411, 425, 427, 436
See application file for complete search history.

(56) References Cited

U.S. PATENT DOCUMENTS

| | | | |
|---|---|---|---|
| 5,553,112 A * | 9/1996 | Hardy et al. | 378/206 |
| 6,754,374 B1 * | 6/2004 | Miller et al. | 382/128 |
| 7,428,318 B1 | 9/2008 | Madsen et al. | |
| 7,552,368 B2 | 6/2009 | Kim et al. | |
| 2002/0065461 A1 * | 5/2002 | Cosman | 600/426 |
| 2005/0190972 A1 | 9/2005 | Thomas et al. | |
| 2008/0303911 A1 | 12/2008 | Madsen et al. | |

OTHER PUBLICATIONS

Comport et al., "Real-Time Markerless Tracking for Augmented Reality: The Virtual Visual Servoing Framework" IEEEE Trans Visual. Comp. Graph. 12(4), 615-628 (2006).

* cited by examiner

Primary Examiner — Peter Luong
(74) Attorney, Agent, or Firm — Siber Law, LLP; Victor Siber; Andres Arrubla

(57) ABSTRACT

Disclosed are methods and systems for guiding emissions to a target. The methods and systems utilize, in part, Markerless Tracking software to detect a beam of energy, such as a laser, toward a target such as a tissue that is the subject of a medical procedure.

37 Claims, 2 Drawing Sheets

METHODS AND SYSTEMS FOR GUIDING AN EMISSION TO A TARGET

FIELD OF THE INVENTION

The disclosure relates to the field of emission technology. More particularly, the disclosure pertains to guiding an emission to a target.

BACKGROUND

Emission devices, such as lasers, require mechanisms to guide an emission to a target. There are several limitations to prior art devices regarding how they direct an emission to a target. For instance, typical prior art camera laser calibration requires the position of the camera relative to the calibration object to be known. In addition, when an object is used to calibrate the laser, the geometry of the object must be known. Moreover, many of these systems do not have real-time feedback to correct errors in targeting the emission device to the target.

There is a need for systems having improved direction of emissions to targets. In particular, there is a need for improved targeting of emissions in medical applications. There is, therefore, a need for new systems that allow for the use of algorithms to calibrate the direction of an emission to a specific location on a target and to provide feedback to correct any errors relating to the direction of the emission.

SUMMARY

The present invention is based, in part, upon the discovery that emission devices can be directed using "Markerless Tracking" software and information relating to the relative pose of an imaging device and an emission device. Markerless tracking algorithms are known in the art and have been described previously (see U.S. Pat. No. 7,428,318, incorporating herein by reference the portion of said patent's disclosure entitled, "Markerless Tracking;" U.S. Pub. No. 2005/0190972, incorporated herein by reference; and Comport et al. *IEEE Trans Visual. Comp. Graph.* 12(4); 615-628 (2006), which is also incorporated herein by reference). This discovery has been exploited to provide systems and methods for directing emissions, such as lasers to a target. In addition, methods and systems are disclosed herein comprising feedback mechanisms to correct for any errors in the targeting of the laser.

Aspects of the methods provide directing an emission to a target on a three-dimensional object. The methods comprise generating a model of the three dimensional object and using an imaging device to generate real-time imagery of the three dimensional object.

Other aspects of the methods described herein include a method of directing an emission to a target on a tracking object. The method comprises generating a model of the tracking object including the target and using an imaging device to generate real-time imagery of the object. The method also includes determining a position and orientation of the object with respect to the imaging device by aligning the model and the real-time imagery, determining a position and orientation of an emission device with respect to the imaging device, and directing an emission from the emission device to the target.

In certain embodiments, the method also comprises determining the position and orientation of the emission device with respect to the imaging device. The method further comprises calibrating the relative pose of the imaging device to the emission device by treating the emission device as a pin-hole camera. In particular embodiments, the method further comprises calculating the relative pose by identifying a pixel position of one or more emission spots visible to the imagery device on the tracking object and determining an emission direction of the emission device, each emission direction corresponding to the pixel position of each emission spot.

In more specific embodiments, the model is a wireframe model. In particular embodiments, the wireframe model is rigid or compliant. In more particular embodiments, the determining a position and orientation of the tracking object relative to the imaging device comprises aligning the wireframe model to an image of the object to generate a keyframe. In still more particular embodiments, the wireframe model is considered correctly aligned to the real-time imagery when it matches the alignment shown in the keyframe. In even more particular embodiments, the wireframe model is aligned with real-time imagery of the object by identification of surface features on the object. In still more particular embodiments, the target is tracked in real-time using the position and position and orientation of the wireframe model in the camera coordinates.

In certain embodiments, the target is a location in the object which is specified as a location in the wireframe model. In other embodiments, the target is visible on the surface of the object. In still other embodiments, the target is not visible on the surface of the object.

In some embodiments, the method further comprises observing the emission on the object with the imagery device and calculating the error between a desired location of the emission on the object and an observed location of the emission. In still other embodiments, the location of the emission is observed as a pixel location in the image. In more particular embodiments, the error is defined as a vector distance between the desired location and the observed location.

In even more particular embodiments, the method further comprises calculating a feedback correction term whereby the emission device is adjusted to correct for the error in location of the emission. In some embodiments, at least two power levels of the emission device are used with low power level of the emission device for real-time feedback adjustment until the error is below a predetermined threshold level and a high power level of the emission device is used to direct the emission to the target when the error is ascertained to be below the predetermined threshold level.

In some embodiments, the emission device is a laser. In other embodiments, the imaging device is a camera. In still other embodiments, determining the position and orientation of the laser with respect to the imaging device comprises calibrating the relative pose of the imaging device to the laser by treating the laser as a pin-hole camera.

In certain embodiments, the method further comprises calculating the relative pose by identifying a pixel position of one or more laser spots visible to the camera on an object and determining a mirror angle used for directing the laser, each mirror angle corresponding to the pixel position of each laser spot. In particular embodiments, the method further comprises using computer vision algorithms to determine the relative pose.

Aspects described herein relate to a system for directing an emission to a specific location on an object. The system comprises an emission device and an imaging device positioned to view the object. The system also includes logic. For instance, the system comprises logic for generating a model of the object and logic for determining a position and orientation of the object with respect to the imaging device by aligning the model and a real-time imagery. The system also includes logic for determining a position and orientation of the emission device with respect to the imaging device and logic for directing an emission from the emission device to the target.

In certain embodiments, the emission device is a laser. In other embodiments, the imaging device is a camera.

In some embodiments, the system includes logic for calibrating the relative pose of the imaging device to the laser by treating the laser as a camera. In still other embodiments, the system further comprises logic for identifying a pixel position of one or more laser spots visible to the camera on an object and determining a mirror angle used for directing the laser, each mirror angle corresponding to the pixel position of each laser spot. In particular embodiments, the system further comprises logic to implement computer vision algorithms for determining the relative pose.

In certain embodiments, logic for the determining a position and orientation of the object relative to the imaging device comprises aligning the wireframe model to an image of the object to generate a keyframe.

In particular embodiments, all of the logics comprise executable code, the executable code being stored on one or more memory devices.

Aspects described herein also relate to a method of targeting a tissue of a patient with an emission beam. The method comprises using an imaging device to generate a real-time image of tracking tissue of the patient and obtaining a diagnostic scan of the tissue containing the tracking tissue and the targeted tissue. The method also comprises aligning the diagnostic scan to the model to identify the location of the targeted tissue in the model and overlaying the model on a real-time imagery of the tracking tissue. The method further comprises determining a position and orientation of an emission device with respect to the imaging device and directing an emission beam to the location of the targeted tissue based on the model alignment with the imagery of the tracking tissue.

In certain embodiments, tracking tissue refers to visible tissue used for tracking. In particular embodiments, the tracking tissue is the same as the targeted tissue.

In certain embodiments, the energy beam is a laser. In particular embodiments, the imaging device is a camera. In more particular embodiments, the tissue is a body part, an organ, or a tissue of a subject.

In certain embodiments, the model is a wireframe model. In more certain embodiments, the wireframe model is aligned with the real-time imagery of the tracking tissue by identification of surface features on the tissue. In still more certain embodiments, a diagnosis of the targeted tissue is performed using information obtained from the emission beam. In even more certain embodiments, the tissue is a tissue requiring treatment. In some embodiments, the tissue that is targeted is normal tissue. In other embodiments, the tissue that is targeted is a lesion.

BRIEF DESCRIPTION OF THE FIGURES

The foregoing and other objects of the present invention, the various features thereof, as well as the invention itself may be more fully understood from the following description, when read together with the accompanying drawings in which.

DETAILED DESCRIPTION

Figure 1:
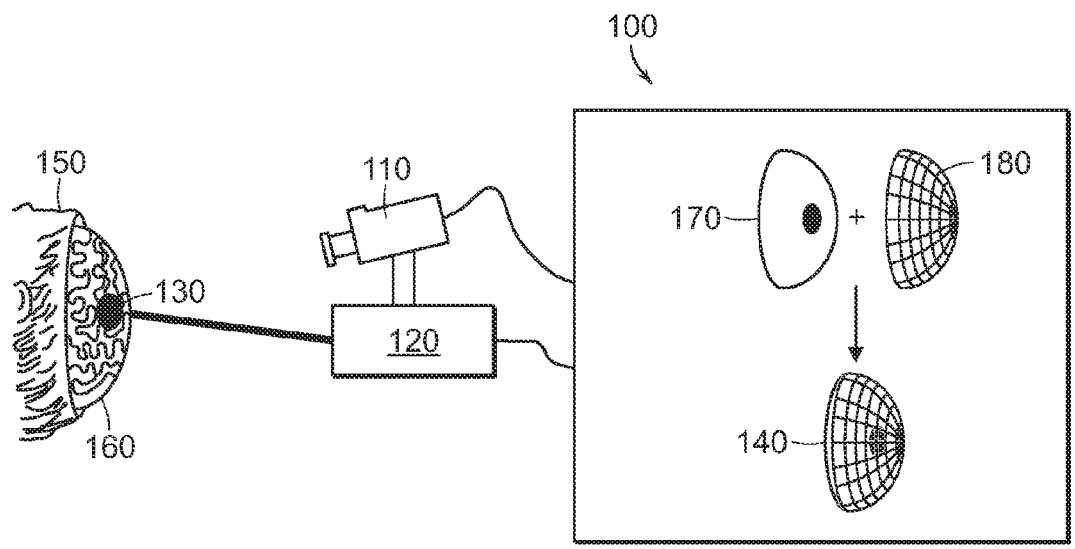
FIG. 1 is a diagrammatic representation showing the organization of the hardware and logic for a representative system used to direct an emission to a target tissue in the brain of a patient.

The issued US patents, allowed applications, published foreign applications, and references, that are cited herein are hereby incorporated by reference in their entirety to the same extent as if each was specifically and individually indicated to be incorporated by reference. Patent and scientific literature referred to herein establishes knowledge that is available to those of skill in the art.

1.1. General

Methods and systems are disclosed for directing an emission to a target on a tracking object. As used herein, the term "tracking object" means a 2- or 3-dimensional object that is observed by an imaging device and whose position and orientation is computed by means of markerless tracking. The methods comprise generating a model of the tracking object including a target and using an imaging device to generate real-time imagery of the object. The method also includes determining a position and orientation of the object with respect to the imaging device by aligning the model and the real-time imagery. In addition, a position and orientation of an emission device is determined with respect to the imaging device. An emission is directed from the emission device to the target. The model described above allows for the relative position and orientation of an object to be tracked. The tracking occurs because the model is positioned relative to the object and utilizes the shape of the object. In such a system, the texture can vary from object to object so long as the shape of the object remains similar. This is useful for biological objects where the shape of anatomy is the same but the texture varies (e.g. retina).

In addition, the methods comprise determining a position and orientation of the object with respect to the imaging device. The methods comprise aligning the model and the real-time imagery. The method also comprises determining a position and orientation of an emission device with respect to the imaging device. The methods also comprise directing an emission from the emission device to the target.

Software available from companies such as Total Immersion is used to implement the tracking algorithms described above. A version of this tracking software is Markerless Tracking Markerless Tracking("MLT") software. MLT uses a representative wireframe model and its alignment to the target in a keyframe to track the position and orientation of the object using natural feature points. As used herein, a "keyframe" is an image of the tracking object and the wireframe that shows proper alignment of the wireframe model to the tracking model. The methods and systems disclosed herein use Markerless Tracking to allow an emission to be directed to a specific location on an object that is tracked. This can be of significant importance for industrial and medical applications.

The emission device can be a laser, an X-ray device, focused ultrasound, electron gun (like in a CRT monitor), water jet, and air jet. Accordingly, representative emissions useful in the present methods include, but are not limited to, laser emissions, X-rays, visible light, coherent light, liquid, ultrasound, sound, thermal emission, and infrared light.

The methods described herein use one or more imaging devices. In particular embodiments, the imaging device is a camera, Optical Coherence Tomography, B-Scan, scanning laser microscope, scanning laser opthalmoscope, directional microphone, and directional infrared sensors, industrial welding robots, automatic tattoo removal, surface etching, micromachining, weapons targeting, and robot navigation In certain nonlimiting examples, the methods comprise computing the position and orientation of the imaging device relative to the emission device by treating the emission device as a pinhole (projective) camera. In treating the emission device as a camera, the methods utilize algorithms originally developed for 2-view geometry to calibrate the emission device (See, e.g., Hartley and Zisserman, *Multiple View Geometry in Computer Vision*, Cambridge University Press, March 2004). This is performed by extending the pinhole camera model to emission steering hardware. The pinhole camera concept is well known in the art. In these embodiments, calibration up to scale has only recording pixel locations of the emission (e.g., a spot in the view of the imaging device) and the determining the corresponding emission device's guidance equipment angles to steer the emission on a calibration object of unknown geometry. In a laser example, the guidance equipment is the laser's steering mirrors. The scale ambiguity can be resolved by knowing the depth of one or more point correspondence or the metric relationship between two or more point correspondences. In certain cases, "scale ambiguity" refers to the ambiguity of the scale of the position of the laser with regard to the camera.

The methodology of directing an emission device is accomplished with the use of information that is acquired in the calibration of the device. The pixel location of the emission spot is identified and visible to the imaging device on a calibration object. In some embodiments, the emission device is a laser. In such embodiments, the laser is directed with knowledge of the mirror angle used for directing the laser to the particular location. Each mirror angle corresponds to the pixel position (e.g., point) of each laser spot generated with the particular mirror angle. These point correspondences refer to pairs of pixels and mirror angles. One point correspondence would be (Xc, Yc, $\alpha_L$, $\beta_L$, where $X_c$ and $Y_c$ are a camera pixel, $\alpha_L$ and $\beta_L$ are mirror angles (i.e., $\alpha_L$ is a mirror that steers the laser's emission in a horizontal direction and $\beta_L$ is a mirror that steers the laser's emission in a vertical direction). Again, the calibration process up to scale involves the computer steering the laser to different points on a target (of unknown geometry) and recording pixels and mirror angles. In notable embodiments, the relative pose of the imaging device and the laser (or any emission device) is determined using a computer vision algorithm, such as the 8-point algorithm to initialize a non-linear optimization. These computer vision algorithms are known in the art (see, e.g., Ma, et al., *An Invitation to 3-D Vision: from Images to Geometric Models*, SpringerVerlag, 2003).

The methods and systems also comprise allowing for an object to be tracked in real time. Such tracking is useful when an object moves in a field or the view of the object is adjusted. Furthermore, the methods and systems described herein allow for calculating the error between a desired location of the emission on an object and an observed location of the emission. If an improper calibration occurs, the emission is "off-target" and does not hit its desired location. As such, the emission does not produce its desired effect and much time will be wasted. In the case of surgical procedures, there could also be injury to tissues.

Accordingly, the methods and systems provide mechanisms to correct calibration problems by, for instance, calculating a feedback correction term whereby the emission device is adjusted to correct for the error in location of the emission. Such correction is accomplished using a known projection of the desired treatment area in the camera, as well as the location of the laser spots that are visible to the camera; it is possible to use feedback control to drive the laser to the proper pixel location.

1.2. Systems

Systems for directing an emission to a specific location on a three-dimensional object are also described herein. Systems typically include an emission device and an imaging device. The imaging device is typically positioned to view a tracking object. The tracking object has a target that is the point or region on or in the object to which an emission to direct an emission.

The systems described herein also have logic for generating a model of the tracking object and for determining a position and orientation of the tracking object with respect to the imaging device by aligning the model and a real-time imagery. For example, the systems can comprise logic for determining a position and orientation of the emission device with respect to the imaging device, as well as logic for directing an emission from the emission device to the target. As detailed below for particular embodiments, the emission device can be a laser and the imaging device can be a camera.

In some instances, the systems comprise logic for identifying a pixel position of one or more laser spots visible to the camera on an object, as well as logic for determining one or more mirror angles used for directing the laser, each mirror angle corresponding to the pixel position of each laser spot.

The systems can comprise computer vision algorithms for determining the relative pose of an imaging device and an emission device. For example, the system comprises logic configured to align an image of the target to a wireframe model to generate a keyframe.

The logics in many of these embodiments are executable code stored on one or more memory devices. Memory devices include storage media such as computer hard disks, redundant array of inexpensive disks ("RAID"), random access memory ("RAM"), solid state memory such as flash memory, and optical disk drives. Examples of generic memory devices are well known in the art (e.g., U.S. Pat. No. 7,552,368, describing conventional semiconductor memory devices and such disclosure being herein incorporated by reference).

To further describe the systems described above, the following non-limiting example is provided. Referring to FIG. 1, a system 100 is shown in which a camera 110 (an imaging device in this illustrative description) and laser 120 (the emission device, named "focused energy" device in the figure) are arranged to allow for viewing of a target 130 (tissue in the brain 160 of a patient 150). The system 100 includes a computer 140 that comprises memory to store the logics for performing the tracking, calibration, and feedback functions of the system.

With regard to an example in which a patient has a cancerous brain tumor, healthy tissue to be ablated, or noncancerous growth, a surgeon cannot see the tissue in the brain. A diagnostic scan 170 shows where the target tissue is located. The computer aligns the diagnostic scan to a wireframe model 180, such that the wireframe is overlaid on the patient and the scan location matches the actual target tissue location. This registration can be done by matching the surface features of the brain in the keyframe to surface features shown in the MRI.

MLT uses the texture of the surface of the brain to align the wireframe model 180 to the real time image of the patient. An aiming beam from the emission device is turned on in order to initiate the feedback. Once the aiming beam is pointing at the correct tumor location, the treatment "focused energy" from the emission device is directed to the tumor and ablates the tumor.

1.3. Methodology

Figure 2:
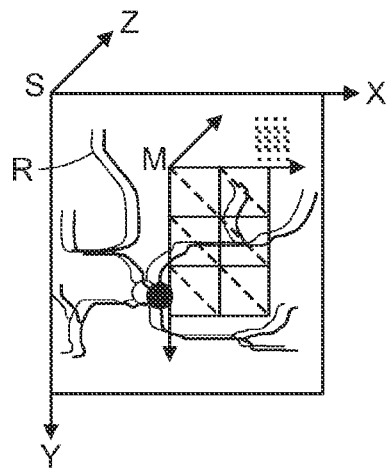
FIG. 2 is a graphical representation showing a camera and laser and their corresponding coordinate system of a camera and laser while producing an alignment of a contour model on a real-time image of a retina.
Figure 2:
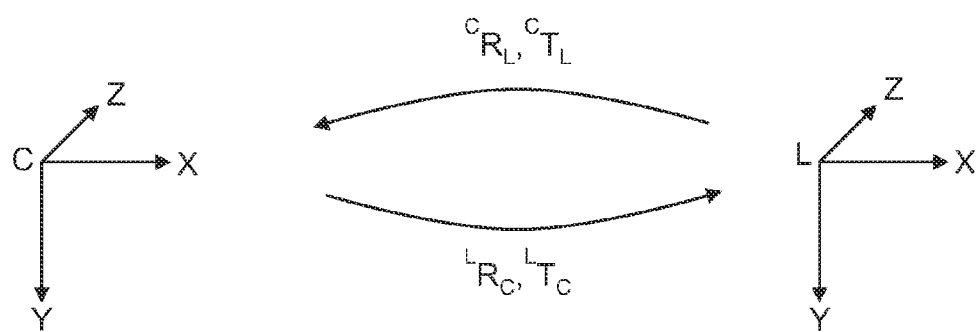

The following example describes how the logics stored in the computer 140 in FIG. 1 provide tracking, calibration, and feedback functions. Referring to FIG. 2, the various components of the system 100 of FIG. 1 are described with respect to a scan and treatment of a retina. Each Component is identified as follows.

FIG. 2 shows the contour model M which is being aligned to the real-time image of the retina R ($R_1$ and $R_C$) via the markerless tracking algorithm. Once the model is aligned, the markerless tracking outputs the position and orientation of the model in the camera coordinates. Since the model is aligned with the real-time image, these coordinates also represent the position and orientation of the retina. The diagnostic scan S is also aligned to the model M such that there is accurate registration of the diagnostic scan to the real-time retina image during tracking. The treatment plan is represented by the pixel matrix in the diagnostic scan. In some embodiments, the diagnostic scan is shown overlaid on the image of the object; the diagnostic scan contains information relating to the treatment plan. Sometimes, the camera C and laser L have a known position and orientation relative to one another due to a priori calibration. The camera C and the laser L are positioned such that the laser can be directed to the retina shown in the real-time image R.

In this example, a system generates a reference location for the laser L to shoot using the alignment of the contour model M with the real-time retina image R and the alignment of the diagnostic scan S with the model M. The system obtains the coordinates of the treatment locations in the diagnostic scan using known coordinate transformations between S, M, C and L generated for the laser L. In certain embodiments, the coordinates for S and M are computed by manual alignment. The determination of C and L coordinates are determined as shown below. The laser L steers the beam such that it passes through the desired location in space. In this configuration, the visual information is used as a reference for the laser servo control. This can be described as a feed-forward visual servo methodology. The following discussion details the coordinate transformations that allow the use of information from MLT to generate the reference coordinates in the laser's L coordinate system.

Any point ($v_i$) represented in a coordinate system attached to object i can be represented as a point $v_j$ in a coordinate system attached to object j via the following transformation, $$v_j = {}^jR_i v_i + {}^jT_i \quad (0.1)$$

Where ${}^jR_i$ represents the orientation of the i-coordinate system in j-coordinates, $v_j$ represents the coordinates of a point in three dimensional space in an i coordinate system, ${}^jR_i$ is in the case of three-dimensional space a 3×3 rotation matrix that represents the orientation of the i-coordinate system in j-coordinates. A rotation matrix is a 3×3 real matrix with det(R)=+1 and $R^TR$=Identity. Similarly, ${}^jT_i$ represents the translation of the i-coordinate system in j-coordinates. Therefore the objective of the reference generation algorithm for the laser delivery is to update the treatment location in the laser coordinates which was originally described in the diagnostic scan coordinates. From equation 0.1 the algorithm computes the following coordinate transformation:

$$v_L = {}^LR_S v_S + {}^LT_S \quad (0.2)$$

${}^LR_S$ and ${}^LT_S$ can be computed by considering a simplified description of the tracking algorithm. The scan and the model are aligned a priori. This is done either manually or automatically. This establishes a fixed coordinate transformation between the scan and the model as (${}^MR_S$, ${}^MT_S$). A keyframe is generated representing proper alignment between the model and a retina image. Then as the real-time image changes, MLT computes the coordinate transformation between the model and the camera such that the model aligns to the real-time image as it did in the keyframe. This is a changing coordinate transformation between the model and the camera at each frame update (${}^CR_M$, ${}^CT_M$). The imaging device and the emission device are then be calibrated such that the coordinate transformation between the camera and the laser is known (${}^LR_C$, ${}^LT_C$). Using equation 0.1 and sequentially representing the treatment locations in the scan, model, camera and finally laser coordinate systems, it can be shown that ${}^LR_S$ and ${}^LT_S$ are given by, $$^LR_S = {}^LR_C {}^CR_M {}^MR_S$$

$$^LT_S = {}^LR_C {}^CR_M {}^MT_S + {}^LR_C {}^CT_M + {}^LT_C$$

The MLT outputs (${}^CR_M$, ${}^MR_S$, ${}^CT_M$, ${}^LT_C$) for the reference generation algorithm. However (${}^LR_C$, ${}^LT_C$) is a relationship between hardware that cannot be computed by MLT. Thus (${}^LR_C$, ${}^LR_C$) is calibrated each time the imaging device and emission device hardware is modified.

1.4 Camera/Laser Pose Computation Using Point Correspondence

Figure 3:
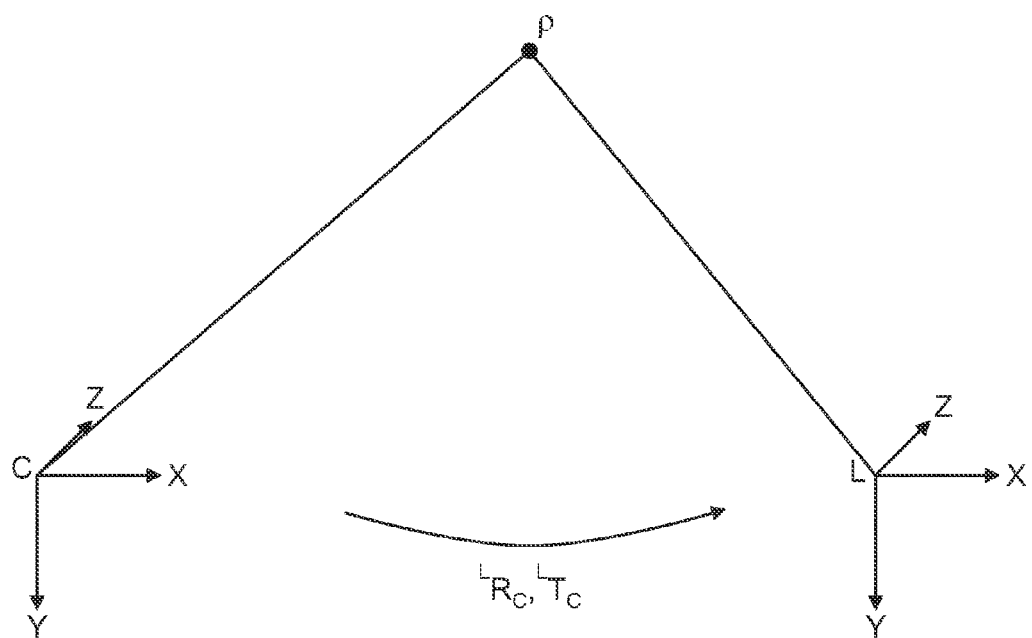
FIG. 3 is a diagrammatic representation showing a point correspondence in which a point in space is simultaneously affected by an emission device which is observed by an imaging device.

The following discussion describes a method involving the identification of a point on an object utilizing imaging locations and steering an emission guidance system to direct an emission to the point. FIG. 3 discusses a certain attribute of the methodology through the use of a representative emission device (i.e., laser) and a representative imaging device (i.e., camera). The following discussion is exemplary and is not limiting.

Consider a laser spot p that is in the field of view of the camera as shown in FIG. 3. The camera C and the laser L are positioned such that the laser L directs a beam to the target and the camera C views the spot p. From equation 0.1, the relationship between the representations of p in each coordinate system is as follows.

$$p_L = {}^LR_C p_C + {}^LT_C \quad (0.3)$$

If $p_L$ and $p_C$ vectors were known, a number of measurements could be taken and (${}^LR_C$, ${}^LT_C$) could be computed directly. However in practice it may not be possible to accurately know the magnitude of $p_L$ and $p_C$ because the object that the laser is shooting is an unknown distance from the camera and the laser. Therefore $p_L$ and $p_C$ are known only up to some unknown scale factor $\lambda_i$.

$$p_i = \lambda_i n_i, \ i=L,C \quad (0.4)$$

where $n_i$ is some vector in the direction of p in i-coordinates. Plugging equation 0.4 into 0.3, the following equation is obtained.

$$\lambda_L n_L = {}^LR_C \lambda_C n_C + {}^LT_C \quad (0.5)$$

In order to solve for (${}^LR_C$, ${}^LT_C$), $\lambda_L$ and $\lambda_C$ is be eliminated. This can be done by multiplying on the left by $[{}^LT_C]_x$, which is the skew symmetric matrix realizing the cross-product in $R^3$ as, $$[{}^LT_C]_x {}^LT_C = {}^LT_C \times {}^LT_C = 0 \quad (0.6)$$

Which gives:

$$\lambda_L [{}^LT_C]_x n_L = [{}^LT_C]_x {}^LR_C \lambda_C n_C \quad (0.7)$$

Since $[^LT_C]_x n_L$ is orthogonal to both $^LT_C$ and $n_L^T$, multiplying on the left by $n_L$ sets the left hand side of equation 0.7 to zero, giving:

$$0 = n_L^T [^LT_C]_x {}^L R_C n_C = n_L^T E n_C. \quad (0.8)$$

Equation 0.8 is the well known epipolar constraint commonly encountered in two-view geometry. Here $[^LT_C]_x {}^L R_C$ is the useful matrix E. There are many algorithms to compute E and extract $(^L R_C, {}^L T_C)$ up to scale, given enough measurements of $n_L$ and $n_C$ in general configuration. However, in the typical two-view geometry, $n_L$ and $n_C$ are pixel locations where here $n_L$ is a vector in the direction of the laser which is related to the laser steering mirror angles.

1.5. Feedback

In certain examples, any errors in the desired location of the emission spot and the actual location of the spot are corrected through a methodology such as the method described herein. In this example, a laser is used as an exemplary, non-limiting emission device. The error between the desired location of the laser spot and the actual location of the laser spot is determined in pixels. Through MLT, the desired treatment location is provided, $(x\ y\ z)^T$. The pixel corresponding to the desired treatment location in the camera can be obtained by $$\begin{bmatrix} x' \\ y' \\ z' \end{bmatrix} = K \begin{bmatrix} x \\ y \\ z \end{bmatrix}$$

$$\begin{bmatrix} x_c \\ y_c \end{bmatrix} = \begin{bmatrix} \frac{x'}{z'} \\ \frac{x'}{z'} \end{bmatrix}$$

where K is the well known camera calibration matrix.

The laser pixel location can be obtained by an image processing step. Since the laser spot is much brighter than the rest of the image, one method to accomplish this is to threshold the image such that a binary image is computed showing only the spot. A "center of mass" operation is then performed to give the location of the center of the laser spot. This is one example of an algorithm to extract the pixel location of the laser spot. Alternatively, other algorithms in the field of image processing can perform this task (see, e.g., Jain, *Fundamentals of Digital Image Processing*, Prentice-Hall, Inc., 1989).

The vector between these two points is then calculated and referred to as the error, e. Some feedback law would then be implemented so that the new input to the laser is as follows:

$$u_L = u_{FF} + u_{FB}$$

$$u_{FB} = f(e)$$

Where $u_L$ is the laser actuator input, $u_{FF}$ is the actuator input from the feed-forward section described, and $u_{FB}$ is some feedback correction term that is a function of the error. One feedback correction scheme may be the "so called" integrator.

$$u_{FB,current} = u_{FB,before} + \gamma e$$

Here the feedback correction term is the feedback correction from the image before plus an added term that is proportional to the error in the current image. $\gamma$ is a term that is chosen to ensure stability and performance.

1.6. Therapeutics

In addition, the present methods and systems utilize emissions for improved surgical methods for ablating tissues. The methods comprise using an imaging device to generate a real-time image of a tissue of the patient and obtaining a diagnostic scan of the tissue. In certain embodiments, the tissue is a healthy tissue that is ablated. Sometimes, the tissue contains a lesion. The methods also comprise aligning the diagnostic scan to a model to identify the location of the tissue to be ablated. Sometimes, the tissue is located on the surface of the tissue. In some instances, the tissue to be ablated is located within the tissue. In either case, the model is overlaid on a real-time imagery of the tissue. A determination of the position and orientation of an emission device with respect to the imaging device is made. An emission beam is directed to the location of the healthy tissue or lesion based on the model alignment with the imagery of the tissue, thereby treating the lesion.

In these methods, any tissue can be treated. In some instances, the target for the laser is a tissue lesion. Tissue lesions include, but are not limited to, tumors, metastatic cancer, noncancerous growths, bacterial infections, viral infections, fungal infections, scar tissue, and aberrant tissue growths. In certain embodiments, such lesions are located in a body part, such as a leg or arm, in an organ, such as the brain, liver, heart, lung, stomach, or eyes, or in a tissue, such as lymph nodes or bone marrow, of a subject.

As with methods described above, keyframes are generated by aligning an image of the target to a model such as, for example, a wireframe model. The image can be a diagnostic scan (e.g., PET scan, MRI), a picture of the tissue, and any other medical scan. For surgical applications, a keyframe can be generated a priori by registering the model to a previously acquired diagnostic scan or image taken prior to surgery.

The emission can be utilized in a medical procedure where specific locations on anatomical structures are targeted and ablated using the emission.

EQUIVALENTS

Those skilled in the art will recognize, or be able to ascertain, using no more than routine experimentation, numerous equivalents to the specific compositions and procedures described herein. Such equivalents are considered to be within the scope of this invention, and are covered by the following claims.

What is claimed is:

1. A method of directing an emission to a target on a tracking object, the method comprising:
   generating a wireframe model of the tracking object including the target;
   generating real-time imagery of the object using an imaging device;
   aligning the wireframe model and the real-time imagery to determine a position and an orientation of the object with respect to the imaging device;
   determining a position and an orientation of an emission device with respect to the imaging device;
   directing the emission from the emission device to the target, wherein the emission is configured to include at least two power levels including a first-low power level for real-time feedback adjustment and a second high power level used to direct the emission to the target;
   observing the emission on the target with the imaging device; and
   calculating an error between a desired location of the emission on the target and an observed location of the emission.

2. The method of claim 1, wherein the step of determining the position and the orientation of the emission device with respect to the imaging device further comprises: calibrating a relative pose of the imaging device to the emission device by treating the emission device as a pin-hole camera.

3. The method of claim 2 further comprising:
calculating the relative pose by identifying a pixel position of one or more emission spots visible to the imaging device on the tracking object and determining an angle of the emission device to the one or more emission spots visible to the imaging device.

4. The method of claim 1, wherein the step of generating the wireframe model further comprises: generating a rigid or a compliant wireframe model.

5. The method of claim 1, wherein the step of determining the position and the orientation of the object with respect to the imaging device further comprises aligning the wireframe model to an image of the object to generate a keyframe.

6. The method of claim 5, additionally comprising: determining that the wireframe model is aligned to the real-time imagery when it matches the alignment in the keyframe.

7. The method of claim 5, wherein the step of determining the position and the orientation of the object with respect to the imaging device further comprises:
identifying surface features on the object to determine when the wireframe model is aligned with real-time imagery of the object.

8. The method of claim 7, additionally comprising: tracking the target in real-time using, the position and the orientation of the wireframe model with respect to the imaging device.

9. The method of claim 8, wherein the step of tracking the target further comprises: tracking a location of the object specified in the wireframe model.

10. The method of claim 9, wherein the step of tracking a location in specified in the object specified in the wireframe model further comprises: tracking the target using a location that is visible on the surface of the object.

11. The method of claim 9, wherein the step of tracking a location in specified in the object specified in the wireframe model further comprises: tracking the target using a location that is not visible on the surface of the object.

12. The method of claim 1, wherein the step of observing the emission on the target comprises: observing the location of the emission as a pixel location in the image.

13. The method of claim 1, wherein the step of calculating an error comprises: determining a vector distance between the desired location and the observed location.

14. The method of claim 1, further comprising calculating a feedback correction term whereby the emission device is adjusted to correct for the error calculated.

15. The method of claim 1, wherein the step of directing the emission comprises: directing a laser.

16. The method of claim 15, wherein the step of generating real-time imagery of the object comprises: capturing at least one image using a camera.

17. The method of claim 16, wherein determining the position and the orientation of the laser with respect to the imaging device comprises calibrating a relative pose of the imaging device to the laser by treating the laser as a pin-hole camera.

18. The method of claim 16 further comprising calculating a relative pose by identifying a pixel position of one or more laser spots visible to the camera on an object and determining a mirror angle corresponding to the pixel position of each laser spot.

19. The method of either of claim 2 or 18 further comprising using computer vision algorithms to determine the relative pose.

20. A system for directing an emission to a target on an object, comprising:
an emission device;
an imaging device positioned to view the object;
at least one processor in communication with said emission device and said imaging device and configured to execute software code for:
generating a wireframe model of the object;
determining a position and an orientation of the object with respect to the imaging device by aligning the wireframe model and a real-time imagery;
determining a position and an orientation of the emission device with respect to the imaging device;
aligning the wireframe model to a real-time image to generate a keyframe; and
directing an emission from the emission device to the target, wherein the emission includes at least two power levels, the first of the at least two power levels being a low power level emission configured for real-time feedback adjustment and the second of the at least two power levels is a high dower level configured for directing the emission to the target;
observing the emission on the target with the imaging device; and
calculating an error between a desired location of the emission on the target and an observed location of the emission.

21. The system of claim 20, wherein the emission device is a laser.

22. The system of claim 21, wherein the imaging device is a camera.

23. The system of claim 20, wherein the at least one processor is further configured to execute software code for:
calibrating a relative pose of the imaging device to the laser.

24. The system of claim 23, wherein the at least one processor is further configured to execute software code for:
identifying a pixel position of one or more laser spots visible to the camera on an object; and
determining a mirror angle corresponding to the pixel position of said one or more laser spots.

25. The system of claim 24, wherein the at least one processor is further configured to execute software code for:
determining a relative pose.

26. The system of claim 20, wherein the executable software code is stored on one or more memory devices in communication with said at least one processor.

27. A method of targeting a tissue of a patient with an emission beam, the method comprising:
generating a real-time image of a tracking tissue of the patient by using an imaging device;
generating a wireframe model of the tracking tissue including the target tissue;
obtaining a diagnostic scan of the tissue containing the tracking tissue and the targeted tissue;
aligning the diagnostic scan to the wireframe model to identify the location of the targeted tissue in the wireframe model;
overlaying the wireframe model on a real-time imagery of the tracking tissue;
determining a position and an orientation of an emission device with respect to the imaging device;
directing the emission beam to the location of the targeted tissue based on the wireframe model alignment with the real-time imagery of the tracking tissue, wherein the emission is configured to include at least two bower levels including a first-low power level for real-time feedback adjustment and a second high power level used to direct the emission to the target;

observing the emission on the target with the imaging device; and calculating an error between a desired location of the emission on the target and an observed location of the emission.

28. The method of claim 27, wherein the step of generating the real-time image of the tracking tissue comprises: tracking tissue refers to visible tissue used for tracking.

29. The method of claim 27, wherein the step of generating the real-time image of the tracking tissue comprises tracking the tracking tissue which is the same as the targeted tissue.

30. The method of claim 27, wherein the step of directing the emission beam comprises: directing a laser.

31. The method of claim 27, wherein the step of obtaining a real-time image comprises: capturing an image using a camera.

32. The method of claim 27, wherein the step of directing the emission beam comprises: directing the emission to a body part, or an organ of a subject.

33. The method of claim 27, wherein the step of overlaying the wireframe model on the real-time imagery comprises: identifying surface features on the tissue.

34. The method of claim 27, additionally comprising: diagnosing the targeted tissue using information obtained from the emission beam.

35. The method of claim 27, wherein the step of directing the emission beam comprises: directing the emission bean to a tissue requiring treatment.

36. The method of claim 35, wherein the step of directing the emission beam comprises: directing the emission bean to normal tissue.

37. The method of claim 35, wherein the step of directing the emission beam comprises: directing the emission bean to a lesion.

* * * * *